United States Patent [19]

Van Velthuijsen

[11] Patent Number: 5,531,983
[45] Date of Patent: Jul. 2, 1996

[54] ORAL HYGIENE PREPARATION

[75] Inventor: John A. Van Velthuijsen, Gorinchem, Netherlands

[73] Assignee: Purac Biochem B.V., Gorinchem, Netherlands

[21] Appl. No.: 305,808

[22] Filed: Sep. 13, 1994

Related U.S. Application Data

[63] Continuation of Ser. No. 39,225, May 10, 1993, abandoned which is a continuation of PCT/NL91/00192, Oct. 8, 1991.

[30] Foreign Application Priority Data

Oct. 8, 1990 [NL] Netherlands ............................ 9002184

[51] Int. Cl.⁶ ............................... A61K 9/16; A61K 9/18
[52] U.S. Cl. .................... 424/49; 424/52; 424/57
[58] Field of Search ........................... 424/49–58

[56] References Cited

U.S. PATENT DOCUMENTS

| | | | |
|---|---|---|---|
| 3,124,506 | 3/1964 | Holman . | |
| 3,873,694 | 3/1975 | Kawig | 424/127 |
| 3,961,004 | 6/1976 | Nasir et al. | 264/115 |
| 4,080,440 | 3/1978 | DiGiulio et al. | 424/52 |
| 4,096,241 | 6/1978 | Geistlich et al. | 424/54 |
| 4,348,381 | 9/1982 | Gaffar et al. | 424/52 |
| 4,397,837 | 8/1983 | Raaf et al. | 424/52 |
| 4,405,600 | 9/1983 | Besic | 424/57 |
| 4,532,124 | 7/1985 | Pearce | 424/52 |
| 4,740,380 | 4/1988 | Melachouris et al. | 426/590 |
| 4,765,984 | 8/1988 | Vellekoop et al. | 424/441 |
| 4,812,303 | 3/1989 | Iorio | 424/44 |
| 4,847,086 | 7/1989 | Knappwust | 424/687 |
| 4,861,590 | 8/1989 | Grodberg | 424/602 |
| 4,867,989 | 9/1989 | Silva et al. | 426/5 |
| 5,145,668 | 9/1992 | Chow et al. | 424/52 |

FOREIGN PATENT DOCUMENTS

| | | | |
|---|---|---|---|
| 0074082 | 3/1983 | European Pat. Off. . | |
| 0089136 | 9/1983 | European Pat. Off. | 424/52 |
| 0162574 | 11/1985 | European Pat. Off. . | |
| 0200323 | 11/1986 | European Pat. Off. . | |
| 3303937 | 6/1984 | Germany | 424/52 |
| 249850 | 9/1987 | Germany | 424/52 |
| 929351 | 6/1963 | United Kingdom | 424/49 |
| 1480594 | 7/1977 | United Kingdom | 424/49 |
| 89/05628 | 6/1989 | WIPO | 424/57 |
| 9010435 | 9/1990 | WIPO . | |

*Primary Examiner*—Shep K. Rose
*Attorney, Agent, or Firm*—Bachman & LaPointe

[57] ABSTRACT

The invention relates to an oral hygienic preparation for combating tartar formation, which preparation comprises a physiologically acceptable medium, containing, incorporated therein, an effective amount of a substance which inhibits the formation of tartar. The substances to be used according to the invention are calcium lactate, calcium lactophosphate and the double salts of calcium lactate like the calcium sodium lactate double salt. Preferably calcium lactate is used as the tartar formation-inhibiting substance.

5 Claims, No Drawings

ORAL HYGIENE PREPARATION

This is a continuation of U.S. application Ser. No. 08/039,225 filed on May 10, 1993, now abandoned, which is a continuation of PCT/NL91/00192, filed Oct. 8, 1991.

The invention relates to an oral hygiene preparation for combating tartar formation, which preparation comprises a physiologically acceptable medium containing, incorporated therein, an effective amount of a substance which inhibits the formation of tartar.

As is generally known, tartar, which occurs in 40–95% of adults and even in children, plays a decisive role in the course and the progression of parodontitis, that is to say inflammation of the gums and the bone in which the teeth are fixed. Tartar impedes the removal of dental plaque and consequently interferes with the prevention and healing of the parodontium. Studies have shown that removal of tartar leads to a distinct improvement in the health of the parodontal tissue (Lindhe, Textbook of Clinical Periodontology, Munksgaard, 1983). For this reason, studies have been carried out on an extensive scale to find agents which are able to inhibit tartar formation.

The anti-tartar agents most widely used nowadays are pyrophosphates. However, the major disadvantage of pyrophosphates lies in the fact that they do not selectively inhibit tartar formation and, moreover, counteract the remineralisation of tooth enamel. This is because the action of pyrophosphates is based on inhibition of crystal growth (Fleisch and Russell, J. Dent. Res. 51, Suppl.2: 324–332, 1972; Mandel et al., Compend. Contin. Educ.Dent. Suppl. 8: 235–241, 1987). For this reason pyrophosphates can therefore even be regarded as potentially caries-promoting (Ten Cate and Simons, Caries Res. 23: 118–119, 1989, Abstract 104). For this reason, generalized use of pyrophosphates in toothpaste is encountering increasing resistance. Extensive studies have been carried out and are still under way in order to counteract this adverse effect of pyrophosphates by means of additives of all sorts and types, such as sodium fluoride, specific polymers, sodium monofluorophosphates, and the like.

U.S. Pat. No. 3,124,506 relates to compositions which are effective as dentifrice and as prophylactic composition for nose and throat and are based on the presence therein of malic acid or certain salts thereof. When employed in a dentifrice malic acid is effective as a tartar removing agent (column 1, lines 22–24). U.S. Pat. No. 3,124,506 further relates to dentifrices and prophylactic nasal and throat compositions containing both malic acid and a salt of lactic acid, preferably calcium lactate. Apparently the simultaneous application of malic acid and calcium lactate involves a synergistic action between these two components, resulting a.o. in an enhancement of the removal of mucous and salivary plaques from the teeth (column 1, lines 38–50). Therefore, compositions according to U.S. Pat. No. 3,124,506 mendatory contain malic acid or a salt thereof, whereas the presence of a salt of lactic acid is merely optional.

Surprisingly, it has been found that the compounds calcium lactate, calcium lactophosphate and double salts of calcium lactate, which are distinctly different from pyrophosphates, possess a tartar formation-inhibiting action.

The invention therefore relates to oral hygiene preparations for combating tartar formation, which preparations comprise a physiologically acceptable medium containing, incorporated therein, an effective amount of calcium lactate, calcium lactophosphate and/or a double salt of calcium lactate as the tartar formation preventing agent, with the proviso that no malic acid or salt of malic acid is present in the oral hygiene composition.

With respect to the above it is brought to the fore that WO 90/10435 relates to a packaged multi-component fluoride dentifrice product comprising at least two separate compartments, wherein the first compartment contains a first component consisting of a stable non-toxic calcium salt, like calcium chloride, calcium acetate, calcium burylate, calcium salicylate, calcium lactate or combinations thereof, preferably calcium chloride (see all the examples), and a non-reactive carrier and wherein the second compartment contains a second component consisting of a stable, non-toxic readily hydrolyzable complex fluoride compound like fluorosilicate, fluorostannate, fluorozirconate, fluoroborate, fluorophosphate or combinations thereof, preferably fluorosilicate as well as a buffer and a non-reactive carrier. Both above-defined compartments are configured in such a way that the contents of the first and the second compartment may be mixed upon dispensing, resulting in a rapid hydrolysis of the fluoride compound and preparation of calcium fluoride. Therefore the role of the soluble calcium salt, preferably calcium chloride, is merely directed to the provision of a source of the calcium ions for the calcium fluoride preparation, i.e. the anionic part of the soluble calcium salt is not considered important.

In EP-A- 0 200 323 an oral hygiene composition is disclosed comprising a silica base, from 1 to 10% by weight of the composition of a water-soluble non-toxic strontium salt, a fluoride source providing from 250 ppm to 2000 ppm of fluoride in the composition and a dentally acceptable carrier provided that when the strontium salt is other than strontium acetate, the silica base has a BET surface area of from 50 to 400 $m^2/g$. The fluoride source may comprise a non-ionic fluorine compound like sodium monofluorophosphate. Further no mention is made of the presence of a lactic acid compound like calcium lactate.

EP-A- 0 162 574 relates to oral hygiene compositions containing an effective concentration of a pharmaceutically acceptable fluoride salt and a pharmaceutically zinc salt, a buffering agent and having a pH of from 3.5 to 6.0. The fluoride salt may be a non-ionic fluorine compound such as sodium monofluorophosphate. Further EP-A- 0 162 574 does not disclose or suggest the use of a lactic acid compound like calcium lactate in the oral hygiene compositions in question.

For the sake of completeness it is pointed out, that the action of calcium lactate as anti-caries agent is known per se from animal experiments. In these studies calcium lactate was added to the diet of test animals; see McClure (J. Nutr. 72. 131–136, 1960), Shrestha et al., (Caries Res. 16.12–17, 1982), van der Hoeyen (Caries Res. 19, 268–370, 1985) and Lembke et al., (Z. Stomatol. 85, 251–261, 1988). All studies showed that in the case of diets containing calcium lactate, the formation of caries occurred to a lesser degree than in the case of the control diets without calcium lactate.

In vitro studies by Shrestha et al. (Caries Res. 16, 12–17, (1982)) showed that the addition of calcium lactate to diets retarded demineralisation, that is to say decalcification of dental enamel by caries-promoting foodstuffs. In clinical demineralisation trials Brudevold et al., (J. Dent. Res. 64, 24–27 (1985)) also found that less demineralisation of dental enamel occurred if 5% by weight of calcium lactate was added to a 10% by weight sugar solution. It was also found that the use of calcium lactate on oral administration as a wash liquid showed an increase in the Ca and P contents in dental plaque (Van der Hoeyen et al., Caries Res. 23, 146–150, (1989)).

The caries-inhibiting effect of calcium lactate which has been indicated above can probably be explained by the increase in the Ca and P contents of dental plaque. As a consequence the acid-buffering effect of the dental plaque increases, so that the pH-drops which cause caries are prevented (see also PCT application PCT/DE88/00778; Knappworst, ZWR 94: 490–496, 1985). The tooth surface will therefore not decalcify (demineralise). Moreover, the remineralisation of the dental enamel is inhibited by the so-called "common ion" effect (Brudevold et al., J. Dent. Res. 64; 24–27, 1985); it is assumed that Ca and phosphate ions in the dental plaque inhibit the dissolution of the complex calcium phosphate of the hard tooth tissue (enamel, cementum or dentin).

In the light of the above it is emphasized that the anti-tartar effect according to the invention of, inter alia, calcium lactate must be regarded as very surprising. After all, on the basis of the increase in the Ca and P contents in dental plaque, which Ca and P are bonded to the organic matrix of the dental plaque, a tartar-promoting effect is obvious (see Ashley, Archs Oral Biol. 20: 167–170, 1975). This is because tartar or calculus predominantly consists of calcium phosphates such as calcium hydroxyapatite, octacalcium phosphate, whitlockite, brushire and magnesium-containing tricalcium phosphate. Newly-formed tartar contains about 50% by weight of brushire. As the tartar ages, the contents of more complex calcium phosphates increase. Hydroxyapatite is the last stage in tartar formation (Mandel. Compend. Contin.Educ.Dent.Supp. 8: 235–241, 1987).

The physical consistency of the oral hygiene preparation according to the invention can be fluid, gel-like or solid. Examples of oral hygiene preparations which may be mentioned are, inter alia, toothpaste, chewing gum and mouthwash. General information with regard to composition and the like of a preparation of this type is given in the book: Pader M., "Oral Hygiene Products and Practice", Marcel Dekker, New York. 1988.

Of the active substances according to the invention, calcium lactate is advantageously used. Specifically calcium-lactate is a virtually tasteless substance which is very suitable for use in the mouth. Moreover, this last-mentioned compound is non-suspect from the pharmacological standpoint and is already used for other pharmacological effects. Thus, calcium lactate is used in calcium tablets for pregnant women.

Furthermore, studies carried out by the Applicant have shown that calcium lactate does not have an adverse effect on the total number of bacteria or on the numbers of *Actinomyces viscosus/naeslundii, A. odontolyticus, Streptococcus sanguis, Streptococcus mutens,* Capnocytophaga spp. or lactobacilli in dental plaque and saliva.

Apart from calcium lactate, calcium lactophosphate and double salts of calcium lactate, such as the CaNa lactate double salt, are also useable as tartar formation-inhibiting substance in the preparations according to the invention.

The amount of active substance in the oral hygiene preparations can vary within wide limits, such as from 0.1 to 99%, based on the weight of the total preparation Advantageously, an amount of 1–10%, based on the total weight of the total preparation, such as toothpaste, is used. On the other hand, the preparations according to the invention can have a solid consistency, such as the form of a lozenge or foaming tablet, in which the amount of active substance is 1–99%, based on the weight of the total preparation.

A preparation according to the invention preferably also contains a non-ionic fluorine compound, such as sodium monofluorophosphate (MFP), because the spectrum of action of the preparation is enlarged by this type of compound. A fluorine compound of this type serves as additional reinforcement of the hard dental tissue against decalcification. The fluorine compound concerned is preferably present in a concentration of 0.1–1.0%. based on the weight of the total preparation.

In addition to a non-ionic fluorine compound, gingivitis-inhibiting agents such a Triclosan® and chlorhexidine can also be incorporated in the preparation according to the invention. Furthermore, conventional additives can be used, such as flavorings, odorants, colorants, preservatives and gelling agents. etc.

The invention is illustrated in more detail in the following examples.

EXAMPLE I

The use of calcium lactate in a mouthwash to inhibit the formation of tartar and to increase the Ca and P contents in the dental plaque.

A calcium lactate solution which contained 5% by weight of calcium lactate was prepared by dissolving the requisite amount of calcium lactate in water. 20 test persons took part in the clinical trial. All test persons cleaned their teeth daily with a commercially available fluoride-containing toothpaste. In a crossover set-up, the test persons rinsed their mouths over a period of 12 weeks with the calcium lactate solution and 12 weeks with water. Between the two periods there was a 2 week interval in which the mouth was not rinsed. At the start of each test period the teeth were cleaned to remove plaque and tartar. During the experiment the test persons maintained the customary oral hygiene. In addition, the mouth was washed with the calcium lactate solution daily at three specific times: 9.00, 13.00 and 22.00 hours. Any teeth cleaning was always carried out before rinsing. Rinsing was carried out using about 10 ml of mouthwash for 20 seconds. The amount of tartar was measured before the experiment and after each experimental period by two investigators working independently of one another. The amount of tartar was determined on the cervical region of the four lower incisors (Schaeken et al., Caries Res. 1990, in press). Tartar is preferentially formed at this location. Immediately after the clinical measurement, plaque samples were collected from each test person and the Ca and P contents of the samples were determined. The tartar scores are shown in Table A.

TABLE A

Tartar formation on the cervical portion of lower incisors after the use of various mouthwashes (average ± SD; n = 18 persons per group)

|  | tartar score |
|---|---|
| baseline* | 4.7 ± 4.6 |
| water | 4.6 ± 4.3 |
| calcium lactate | 2.9 ± 3.4** |

*baseline , at the start of the trial, just before cleaning the teeth
**P<0.05, paired t test On all surfaces measured, the tartar score was lower in the calcium lactate group than at the start of the trial (baseline) or after rinsing with water.

The solids content of the plaque samples and the Ca and P concentrations are shown in Table B.

TABLE B

Solids content (mg) and calcium and phosphate contents (µg/mg solids) in plaque after the use of various mouthwashes (average ± SD; n = 36 per group)

|  | solids content (mg) | calcium (µg/mg) | phosphate (P) (µg/mg) |
|---|---|---|---|
| baseline | 1.50 ± 0.10 A* | 10.8 ± 1.7 A | 5.1 ± 0.5 A |
| water | 1.39 ± 0.10 A | 8.6 ± 0.9 A | 3.9 ± 0.3 A |
| Ca-lactate | 1.56 ± 0.16 A | 24.6 ± 3.1 B | 8.6 ± 2.0 B |

*Averages with the same letter are not significantly different (Tukey test)

After rinsing with a calcium lactate-containing solution in water, the Ca end P concentrations were much higher than in the case of the baseline or after rinsing with water.

EXAMPLE II

The use of calcium lactate in toothpastes for inhibiting tartar formation

Three types of toothpastes having the composition given Table C were made under generally accepted GMP (Good Manufacturing Practice) conditions (Pader M. "Oral Hygiene Products end Practice", Marcel Dekker, N.Y., 1988).

TABLE C

Composition of the experimental toothpastes in grams per kilogram

|  | Control | Ca lactate | Ca lactate/ Na lauryl sulphate |
|---|---|---|---|
| glycerol 85%* | 130 | 120 | 120 |
| Carbohydroxymethyl cellulose, moderate viscosity | 30 | 30 | 30 |
| Na benzoate | 6 | 6 | 6 |
| Na monofluorophosphate | 1 | 1 | 1 |
| water | 482 | 422 | 412 |
| CaHPO$_4$.2H$_2$O | 350 | 350 | 350 |
| peppermint oil | 1 ml | 1 ml | 1 ml |
| calcium lactate.5H$_2$O | — | 70 | 70 |
| Na lauryl sulphate | — | — | 10 |
|  | 1000 | 1000 | 1000 |

85% by weight solution in H$_2$O

Sixty test persons were distributed between three experimental groups. Test persons in the control group cleaned their teeth three times a day for 3 minutes using the control toothpaste. In the two experimental groups, toothpaste which contained 5% calcium lactate (regarded as anhydrous product) plus, if present, 1% sodium lauryl sulphate was used to clean the teeth. The duration of the experimental period was 3 months. The tartar score was recorded at the start and at the end of the experimental period with the aid of the VM tartar index (Volpe et al., Periodontics 5: 184–193, 1967). At the start of the trial, the teeth of each participant were thoroughly cleaned to remove plague and tartar. The tartar scores are given in Table D.

TABLE D

Tartar formation on the lingual surfaces of the lower incisors after use of control toothpaste and calcium lactate toothpaste (V-M tartar index).

|  | Baseline | 3 months | % reduction |
|---|---|---|---|
| control | 1.56 (2.50) | 1.33 (2.15) | 15 |
| calcium lactate | 1.12 (1.99) | 0.75 (0.99) | 33* |
| calcium lactate/ Na lauryl sulphate | 1.19 (1.56) | 0.72 (0.83) | 39* |

*significantly different from the control group (P<0.05, paired t test)

The amount of tartar in the two calcium lactate groups was very much more reduced than in the control group.

I claim:

1. A homogeneous dentifrice toothpaste or mouthwash for combating tartar formation, which consists essentially of: a single homogeneous, aqueous, physiologically acceptable toothpaste or mouthwash medium; and incorporated in said medium in an amount of 1–10% based on total weight of the product, a tartar-formation inhibiting agent selected from the group consisting of calcium lactate, calcium lactophosphate, the double salts of calcium lactate and mixtures thereof, said homogeneous dentifrice toothpaste or mouthwash for combating tartar formation being further characterized by the absence of inorganic fluoride, phosphate, pyrophosphate salt as well as malic acid and any salt of malic acid.

2. Preparation according to claim 1, wherein the preparation contains calcium lactate.

3. Preparation according to claim 1, wherein said preparation is a mouthwash.

4. Preparation according to claim 1, wherein said preparation is a dentifrice toothpaste.

5. Preparation according to claim 1 consisting essentially of said medium and agent.

\* \* \* \* \*